United States Patent [19]

McDonnell

[11] Patent Number: 4,537,195

[45] Date of Patent: Aug. 27, 1985

[54] ELECTRICAL CONTROL OF BODY DISCHARGES AND HEADACHES

[76] Inventor: Roy E. McDonnell, 15 Miller St., O'Connor, Capital Territory 2601, Australia

[21] Appl. No.: 403,497

[22] PCT Filed: Nov. 20, 1981

[86] PCT No.: PCT/AU81/00167

§ 371 Date: Jul. 16, 1982

§ 102(e) Date: Jul. 16, 1982

[87] PCT Pub. No.: WO82/01656

PCT Pub. Date: May 27, 1982

[30] Foreign Application Priority Data

Nov. 20, 1980 [AU] Australia ............................ PE6562

[51] Int. Cl.³ ............................................. A61N 1/36
[52] U.S. Cl. .................................................. 128/422
[58] Field of Search ........... 128/1 C, 419 R, 421–422, 128/639

[56] References Cited

U.S. PATENT DOCUMENTS

| | | | |
|---|---|---|---|
| 3,543,761 | 12/1970 | Bradley | 128/421 |
| 3,640,284 | 2/1972 | DeLangis | 128/422 |
| 3,800,800 | 4/1974 | Garbe et al. | 128/421 |
| 3,870,051 | 3/1975 | Brindley | 128/422 |
| 3,902,502 | 9/1975 | Liss et al. | 128/422 |
| 3,933,147 | 1/1976 | DuVall et al. | 128/421 |
| 3,941,136 | 3/1976 | Bucalo | 128/422 |
| 3,943,938 | 3/1976 | Wexler et al. | 128/421 |
| 3,983,881 | 10/1976 | Wickham | 128/422 |
| 4,106,511 | 8/1978 | Erlandsson | 128/422 |
| 4,147,171 | 4/1979 | Greene et al. | 128/421 |
| 4,153,059 | 5/1979 | Fravel et al. | 128/422 |
| 4,155,366 | 5/1979 | DiMucci | 128/421 |
| 4,227,516 | 10/1948 | Meland et al. | 128/1 C |
| 4,235,241 | 11/1980 | Tabuchi et al. | 128/639 |
| 4,249,537 | 2/1981 | Lee et al. | 128/422 |
| 4,324,253 | 4/1982 | Greene et al. | 128/421 |
| 4,334,525 | 6/1982 | Kastrubin | 128/1 C |

FOREIGN PATENT DOCUMENTS

| | | | |
|---|---|---|---|
| 0061753 | 10/1982 | European Pat. Off. | 128/421 |
| 1489650 | 8/1964 | Fed. Rep. of Germany | 128/1 C |
| 2260564 | 12/1972 | Fed. Rep. of Germany | 128/419 R |
| 725671 | 4/1980 | U.S.S.R. | 128/421 |
| 740253 | 6/1980 | U.S.S.R. | 128/422 |
| 760975 | 9/1980 | U.S.S.R. | 128/1 C |
| 776613 | 11/1980 | U.S.S.R. | 128/1 C |
| 799755 | 1/1981 | U.S.S.R. | 128/421 |

OTHER PUBLICATIONS

A. Winter, "The Use of Transcutaneous Electrical Stimulation (TNS) in the Treatment of Multiple Sclerosis", J. Neurosurgical Nursing, vol. 8, No. 2, pp. 125–131.

G. D. Schuster, "The Use of TENS for Peripheral Neurovascular Diseases", J. Neurological & Orthopaedic Surgery, Jul. 1980, pp. 219–221.

L. E. Edwards, "Device for Control of Incontinence of Urine in Women", British Medical Journal, Jul. 1970.

D. C. Merrill et al., "Urinary Incontinence", Urology, Jan. 1975, vol. V, No. 1, pp. 67–72.

B. R. Hopkinson et al., "Electrical Treatment of Incontinence", Brit. J. Surg., 1967, vol. 54, No. 9, pp. 802–805.

E. S. Glen, "Effective and Safe Control of Incontinence by the Intra-Anal Plug Electrode, Brit. J. Surg., 1971, vol. 58, No. 4, pp. 249–252.

L. Edwards et al., "Investigation and Treatment of Resistant Urinary Incontinence", British Medical Journal, Mar. 1971, pp. 543–545.

B. R. Hopkinson et al., "Electrical Treatment of Anal Incontinence", The Lancet, Feb. 1966, pp. 297–298.

CONTiNAiD Brochure, Mentor Corporation, Minneapolis, Minnesota.

Primary Examiner—William E. Kamm
Assistant Examiner—Mitchell J. Shein
Attorney, Agent, or Firm—Kenway & Jenney

[57] ABSTRACT

Electrical stimulation through externally applied electrodes is used to control discharge from a stoma. The electrical signals applied to the electrodes have a frequency in the range of 10 Hz to 80 Hz, and a voltage level in the range of 20 volts to 60 volts. Apparatus for effecting the electrical stimulation is described. The electrodes may be ECG electrodes or formed as a pair of discs molded into an insulating pad.

10 Claims, 3 Drawing Figures

ELECTRICAL CONTROL OF BODY DISCHARGES AND HEADACHES

TECHNICAL FIELD

This invention concerns the control of certain body functions by electricl stimulation.

In a first application of the present invention, it concerns control of the anus and/or bladder.

In a second application of the present invention, it controls migraine and stress headaches.

In a third aspect, the present invention is used by persons who have had a colostomy or ileostomy operation, so that drainage or discharge from their digestive systems takes place through an opening in the abdominal wall, termed a stoma. In this application of the present invention, it controls discharge from the opening or stoma.

In each case, the control that is provided by the present invention is by means of low frequency electrical stimulation of nerves which govern the action being controlled.

BACKGROUND ART

Consider first the problem of incontinence. Incontinence and other disorders of the anus and bladder functions are major medical problems, particularly in geriatric medicine.

Where incontinence is tolerated, considerable time is spent by nursing staff in regular, almost continuous, changing of a patient's clothes and bedding. However, incontinence is not generally acceptable by a sufferer or the family of a sufferer, and various techniques have been developed to provide some control of incontinence.

Some of these control techniques involve "mechanical" control apparatus. One example of "mechanical" control is the use, with males, of continuous catheterization, with a bag for collection. This has been used for some time, but is an unpleasant solution and is disliked by patients. Another "mechanical" control device, developed for control of urinary incontinence in women by L. E. Edwards (and described in an article in the British Medical Journal, July 1970 issue, at page 104) is a triangular device having a steel wire projection which is curved and is provided with a corrugated plastic pad. The steel wire fits into the vagina and he corrugated pad exerts gentle pressure on the urethra to prevent discharge of urine. This device has not yet received wide acceptance.

Electrical control of the bladder and anus has also been attempted previously. This electrical control has developed in two major ways. One of these is the implantation of electrodes into the flesh of a patient, while the other is the use of rectal tampons which are fitted with electrodes.

The first insertion of electrodes into the pelvic floor by surgery, followed by the application of electrical voltages to the electrodes, is usually attributed to K. P. S. Caldwell, who reported his work in various papers that were published in the early and mid-1960's. More recent reference to this technique is found in the papers by (a) L. Edwards, N. Harrison and J. P. Williams, entitled "Investigation and treatment of Resistant Urinary Incontinence", which was published in the British Medical Journal, in the 6th March 1971 issue, at pages 543–545; and (b) D. C. Merrill, C. Conway and W. deWolf entitled "Urinary Incontinence-treatment with electrical stimulation of the pelvic floor", which was published in Urology, Volume V, January, 1975, at pages 67 to 72.

The latter paper has illustrations of the surgical electrode implantation that is necessary. Both papers refer also to the use of rectal tampons fitted with electrodes, which have been referred to in other publications as "transrectal tampons" and "intra-anal plugs".

The rectal tampon with fitted electrodes was first developed by B. R. Hopkinson and R. Lightwood, and described in their papers published in The Lancet (5th February 1966 issue, pages 297 to 298) and in the British Journal of Surgery (Volume 54, 1967, pages 802 to 805). The successful use of this form of control of incontinence has also been reported by E. S. Glen (in his paper entitled "Effective and safe control of incontinence by the intra-anal plug electrode", which was published in the British Journal of Surgery, Volume 38, 1971, pages 249–252. Recently the anal plug or rectal tampon aid has become available commercially in the U.S.A. (on prescription), being marketed by Mentor Corporation, Minneapolis, under the trade mark "Continaid".

It is interesting to note that notwithstanding the acclaim given to the rectal tampon or anal plug control technique, which uses internal stimulation of the pudendal nerve of a patient but does not require a surgical procedure for its adoption by a patient, Edwards, Harrison and Williams, in their paper referred to above, found a number of sufferers of "resistant urinary incontinence" who refused treatment.

Thus it can be seen that in spite of recent advances in control of incontinence, electrical stimulation of the pudendal nerve, even without surgical procedures, is not accepted in its previously developed form by all sufferers of incontinence.

Turning now to the other aspects of the present invention, the present inventor is unaware of any technique which has been developed for the control of drainage or discharge through a stoma, but does know of the use of electrical treatment of pain.

The electrical treatment of pain is known as transcutaneous electrical nerve stimulation, or "TENS" (sometimes "TNS"). Perhaps the earliest recorded use of TENS was by the Roman physician Scribonius Largus, who used electric ray or torpedo fish for the treatment of headaches. This ancient use of TENS was noted by A. Winter in his paper entitled "The use of electrical stimulation (TNS) in the treatment of multiple sclerosis", which was published in the Journal of Neurosurgical Nursing, Volume 8, December 1976, at pages 125 to 131. TENS has also been described by G. D. Schuster in his paper entitled "The use of TENS for peripheral neurovascular diseases", which appeared in The Journal of Neurological and Orthopaedic Surgery, Volume 1, July 1980, pages 219 to 221. But neither Winter nor Schuster have appreciated that TENS might be of assistance to sufferers of migraine or stress headaches, in the same way as the present invention will be seen to be applicable. Indeed, the brochure which is supplied by Medtronic, Inc. with that company's TENS equipment, refers to the use of TENS in various locations on the body for short-term relief of acute pain, but in its reference (in "appendix C") to control of neuropathic pain in the head, electrodes are placed on the temple and cheek of the patient. There is no suggestion in this brochure that migraine or stress headaches can be controlled by TENS.

Thus, although migraine and stress headaches have been known and experienced for many years (there are references to headaches in the writings of the Babylonian era, and migraine was described in A. D. 81 by a physician, Aretaeus, who practiced in Alexandria), until the present invention was developed there has been no effective control of such headaches. Many techniques have been tried, including acupuncture, the avoidance of certain foods, hypnotherapy and othe psychiatric treatments, but the sufferer usually finds relief, to a degree, in proprietory analgesics, until the headache passes.

DISCLOSURE OF THE PRESENT INVENTION

It is an objective of a first aspect of the present invention to provide a control for the bladder and/or the anus, which is effective, safe, easy to use and economical.

This objective is achieved by providing continuous electrical stimulation through the skin, using a pair of electrodes, to which a low voltage (typically up to 50 volts), low frequency signal (typically a square wave D.C. signal having a frequency in the range from 10 Hz to 40 Hz is applied. The stimulation is applied in a region of the body where the pudendal nerve channel runs closest to the body surface in the case of control of both the anus and the bladder.

Thus, according to a first aspect of the present invention, a method for controlling the operation of (a) the bladder and (b) the anus comprises the steps of (i) applying a pair of electrodes to the skin in the region where the pudendal nerve channel runs near to the body surface; and (ii) applying to the electrodes a continuous electrical signal at a voltage of up to about 50 volts, and at a frequency in the range of from 10 Hz to 80 Hz, preferably in the range of from 20 Hz to 40 Hz.

Typically, the electrode will be a pair of disc electrodes moulded into the surface of an attachment plate or pad of insulating material, adapted to be held against the skin of the user by, for example, micropore tape, or will be electrodes manufactured to be similar to ECG electrodes.

It is an objective of a second aspect of the present nvention to provide a treatment which reduces the frequency of occurrence of migraine and stress headaches.

This objective is achieved by electrical stimulation using low frequency, low voltage signals applied to a cutaneous nerve system between the neck and wrist of a headache sufferer, for periods of between 10 and 15 minutes in the pre-headache stage of ½ hour to 2 hours, in which migraine and stress headache (also known as vascular headache) sufferers receive warnings of their impending headache.

According to a second aspect of the present invention, a method of treating sufferers of migraine and vascular headaches to reduce the frequency of occurrence thereof comprises the steps of (a) applying a first electrode to the skin of the inner forearm of the sufferer, at the side corresponding to the side of the head affected by the migraine or the side of the head most affected by the vascular headache;

(b) applying a second electrode to the acupuncture hot spot of the neck on the same side of the body as the first electrode; and (c) applying an electrical signal having a frequency of from 30 Hz to 70 Hz and a voltage in the range from 30 volts to 80 volts between the first and second electrodes for a period of from about 10 minutes to about 15 minutes.

For control of migraine and vascular headaches, the electrical stimulation is applied as soon as possible at the first sign of the onset of an attack. For the control of vascular headaches, the stimulation is applied when required for a period of at least one month, a longer period of treatment being necessary if the headache persists.

Preferably the frequency of the electrical signal is about 50 Hz, and its voltage is about 60 volts (but both the frequency and voltage may be varied; the voltage required will depend on the skin impedance of a sufferer).

The voltage and frequency of the signal may be varied during a period of treatment, and from one treatment period to another treatment period.

Consider now the person who has undergone a colostomy or ileostomy operation resulting in a stoma on the external abdominal wall. The numbers of such persons are increasing each year, and the percentage of the population in developed countries who undergo such operations increases annually as the average age of the population increases. Unfortunately, as already noted above, there is no known method of controlling discharge from a stoma, and such persons have no alternative but to continuously use a colostomy bag in conjunction with the stoma.

It is an objective of a third aspect of the present invention to provide a control of discharge from the stoma.

This objective is achieved by creating an artificial sphincter muscle around the length of intestine which leads to the stoma and then controlling the contraction of the artificial sphincter muscle by low frequency, low voltage electrical stimulation. Conveniently, the artificial sphincter muscle can be formed from a number of long muscles, extending from the shoulder to the pelvis.

Hence, according to a third aspect of the present invention, a method for controlling discharge from a stoma comprises:

(a) winding a length of muscle around the intestine connected to the stoma in the region adjacent to the stoma;

(b) applying a pair of electrodes to the skin in the region of the length of muscle; and (c) applying to the electrodes a continuous electrical signal at a voltage in the range 20 volts to 60 volts and at a frequency in the range 10 Hz to 80 Hz, whereby the length of muscle is caused to contract around the intestine and effectively prevent discharge through the stoma.

In each aspect of the present invention, the control or treatment can be conveniently effected using a small, portable, battery-powered, control apparatus.

Thus, according to a further aspect of the present invention, apparatus for effecting control or treatment by electrical stimulation comprises:

(a) a pair of electrodes;

(b) a source of low voltage, low frequency electrical signal comprising an oscillator adapted to produce output signals at a frequency in the range 10 Hz to 100 Hz; and (c) means to control the voltage amplitude of the output signals of the oscillator.

Typically the oscillator will be an oscillator which is powered by a battery, and the voltage amplitude control means will be a voltage multiplier, to the output of which the electrodes will be connected. The signal from the oscillator is preferably a square wave D.C. signal.

When applied to the control of incontinence, the electrodes are preferably formed as a pair of disc electrodes moulded into the surface of a plate of the equipment, or comprises a pair of stick-on electrodes of the type used in ECG treatment. A similar electrode arrangement is used to control discharge from a stoma.

In the case of use of the equipment for control of vascular or stress headaches and migraine, the electrodes to be attached to the forearm and skin of the neck are preferably "INTRODE" brand ECG electrodes, type 4612.

Embodiments of the present invention will now be described with reference to the accompanying drawings.

DETAILED DESCRIPTION OF ILLUSTRATED EMBODIMENT

Figure 1:
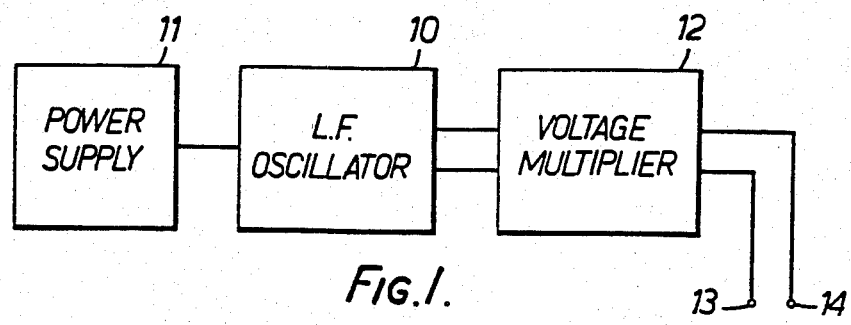
FIG. 1 is a block diagram of one form of the apparatus of the present invention.

Referring first to FIG. 1, variable low frequency variable oscillator 10, capable of generating D.C. pulses, is powered by a D.C. power supply 11 and delivers its output to a voltage multiplier or amplifier 12. The voltage multiplier or amplifier is controllable to produce output signals having a required voltage range, which are supplied to the electrodes 13 and 14. Since the signals supplied to the electrodes are low voltage, low frequency signals, the variable oscillator 10 may be any one of a number of known small battery powered oscillators, producing pulses at a frequency of from 10 Hz to 100 Hz, which are commercially available. The power supply 11 may then be a 9 volt cell (for example, an Eveready cell No. 216) and the oscillator, power supply and voltage multiplier may be mounted on a single circuit board in a small case. Such a case need be fitted with only one external control knob—an output signal level control with an on-off switch built in—as the frequency of the oscillator will usually be preset and require no adjustment.

Figure 2:
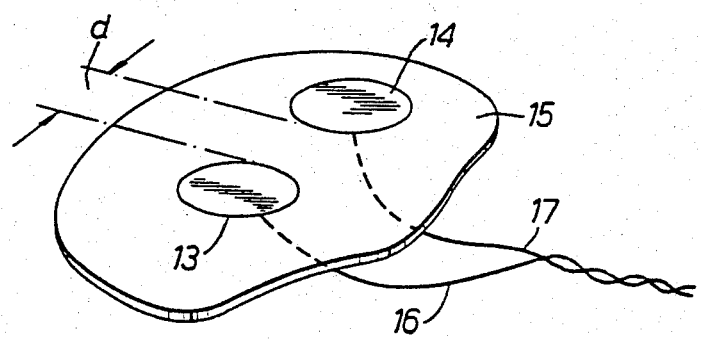
FIG. 2 illustrates an electrode configuration for use in control of incontinence and in control of discharge from a stoma.

The electrodes 13 and 14 may be of any suitable type, but for the control of incontinence, they are preferably formed as discs in a pad as shown in FIG. 2. The electrodes 13 and 14 of FIG. 2 are preferably discs formed on stainless steel or similar inert metal which are set in a plastic pad 15 which can be moulded to any convenient shape. The electrodes are connected to the output of the voltage multiplier 12 by insulated leads 16 and 17. Typically the spacing d of the electrodes is from 4 mm to 15 mm, but this spacing may be up to 50 mm. The actual spacing used depends on the area of stimulation.

In use, to control the operation of the anus, the disc electrodes are applied to the skin in the region of the anus, to either the left or right of the anus, where the pudendal nerve runs closest to the skin. This position may vary from patient to patient, but can be seen from the diagram on page 1002 (FIG. 12-70, entitled "Pudendal nerve, and sacral and pudendal plexus of the right side") of "Gray's Anatomy". When properly located, the pad 15 is suitably moulded to fit the skin in the region of contact and the pad 15, with its electrodes, is held in place, typically with micropore tape. When a signal in the range from 10 Hz to 80 Hz, at a voltage of about 30 volts, is then applied to the electrodes, the pudendal nerve is stimulated to contract the sphincter muscle and close the anal canal. The anal canal will then remain closed for as long as the signal is applied to the electrodes. If the patient wishes to open his bowels, the signal is switched off and the pad is removed. The pudendal nerve is then no longer stimulated and the anus will open normally.

A similar approach is taken to control urinary incontinence, with the electrodes applied to the region of the pudendal nerve as in the control of the sphincter muscle of the anus. It is not necessary to remove the pad after stimulation is switched off to urinate.

A signal in the range 10 Hz to 80 Hz (typically a square wave D.C. signal having an amplitude of about 30 volts, is effective for control of incontinence, but it may be varied, as necessary, to suit a particular patient. For example, the frequency of the signal will usually have to be increased to the higher frequency limits if the incontinent patient has also suffered nerve damage. Such a patient may also require a higher voltage of the control signal. It is, of course, preferred to keep the voltage of the applied signal at the lowest effective value to conserve battery life.

Figure 3:
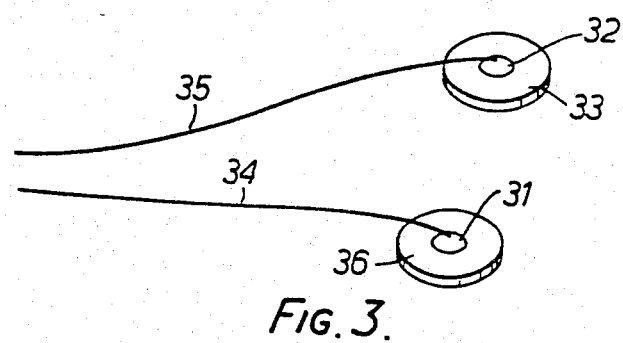
FIG. 3 shows the electrode arrangement for control of migraine and stress headaches.

When the present invention is used to control migraine and stress headaches, the electrodes illustrated in FIG. 3 are used. The electrode 31 is an ECG type of electrode and is held against the inner forearm, immediately above the wrist of a patient, by its adhesive cover or backing 36. This electrode 31 is used as an earthy point for the electronics, and is connected to the negative output of the voltage multiplier 13. Preferably the connection is by a lead 34 which is connected to the unit containing the signal source through a plug-operated power switch. This power switch is normally open circuit, but is closed when the lead plug is inserted. It saves battery life by ensuring the signal source is disconnected when the treatment is not required. The electrode 31 typically has a surface area for contact with the skin of about 3.5 square centimeters (to reduce current density and allow a large coverage of the cutaneous nerve system of the wrist).

The second electrode 32, with its adhesive backing 33, is also an ECG type of electrode. It is connected to the signal supply by lead 35.

Preferably, the connections to electrodes 31 and 32 are by an aligator clip, most preferably of the "NIKO" brand type.

In use, when the migraine sufferer receives the customary warning of the onset of a headache, the carbon pad electrode 31 is adhered to the inside forearm of the sufferer, immediately above the wrist on the side corresponding to the side of the head affected by the migraine. The signal supplied to the electrodes is set to a frequency of about 60 Hz and a peak voltage level of about 50 volts. The aligator clip that will subsequently be attached to the second electrode 32 is then lightly applied to the skin on the affected side of the neck, and moved around until the most sensitive region (known as the "acupuncture hot spot") is located. The signal voltage is then reduced to zero, electrode 32 is applied firmly to the hot spot and the clip is then applied to the electrode 32. The signal voltage is then increased gradually until the stimulation is felt, but below the level of pain. This signal voltage is then applied for a period of from 10 to 15 minutes.

The voltage level may need to be adjusted during the treatment period, to compensate for variation in tissue impedance as a result of the stimulation. Adjustment of the voltage level is preferably by means of an expanded linear output control, with the control lever located immediately outside the casing of the signal source.

It has been found that with a treatment in this manner, when required, over a period of four weeks, most sufferers of stress or vascular headaches report a dramatically reduced intensity of headache, and a significant number of patients have reported complete absence of stress headaches after such treatment.

The reason for such beneficial results is not known, but the present inventor believes it is associated with the stimulation of muscular walls of the large arteries. This stimulation prevents the constriction of these arteries due to tension. Constriction of the arteries reduces the blood flow to the capillary network of the cerebral cortex, which, in turn, causes the capillaries to dilate, thus stretching the nerve endings and causing pain, a feature of migraine and stress headaches.

With regard to control of discharge from a stoma, this aspect of the invention has not been illustrated. However, the present invention, in this aspect, requires the wrapping of a muscle in such a manner as to form an artificial sphincter around the stoma in the abdominal wall or around the intestine leading to the stoma. This may conveniently be effected by disconnecting part of the Rectus Abdominis, Latissimus Dorsi, or similar muscles. The sphincter muscle, so constructed, is then stimulated into contraction using the technique described above for control of incontinence, preferably using the electrode configuration illustrated in FIG. 2, which is adhered to the skin in the region of the Ventral rami thoracic spinal nerve, the Thoracodorsal nerve or similar nerves.

BENEFITS OF THE INVENTION

The benefits of such simple, inexpensive, yet effective controls and treatments will be readily appreciated by medical practitioners, who will also recognise that variations in the methods and apparatus of the present invention may be adopted without departing from the present inventive concept. By using the present invention, not only will personal suffering be alleviated, but many persons whose ability to work has been impaired will be able to become productive members of the workforce again.

Another benefit of the present invention, in its application to the control of incontinence, is that in many cases, control of anal incontinence by stimulation therapy can avoid the need for a colostomy operation. Furthermore, the present invention (applied to anal control) is also of value to persons who have undergone the recently-developed operation known as "ileo-anal pull-through" (for example, to overcome Chrome's disease), who can use electrical stimulation to prevent noctural leakage.

I claim:

1. A method for controlling discharge from a stoma comprising:
    (a) winding a length of muscle around the intestine connected to the stoma in the region adjacent to the stoma;
    (b) applying a pair of mutually spaced electrodes to the skin in the region of the length of muscle; and
    (C) applying to the electrodes a continuous electrical signal at a voltage in the range 20 volts to 60 volts and at a frequency in the range 10 Hz to 80 Hz,
    whereby the length of muscle is caused to contract around the intestine and effectively prevent discharge through the stoma.

2. A method as defined in claim 1 in which the length of muscle is part of the *Rectus Abdominis* or the *Lattissimus Dorsi*.

3. A method as defined in claim 2, in which the electrodes are applied to the skin in the region of the Ventral Rami thoracic spinal nerve or the Thoracodorsal nerve.

4. A method as defined in claim 2, in which the electrodes are a pair of disc electrodes, and are first moulded into the surface of an insulating plate or pad, the plate or pad being subsequently applied to the skin.

5. A method as defined in claim 4, in which the electrodes are independently applied to the skin.

6. A method as defined in claim 5, in which said electrical signal is a D.C. signal having a square wave waveform.

7. A method as defined in claim 1, in which the electrodes are applied to the skin in the region of the Ventral Rami thoracic spinal nerve or the Thoracodorsal nerve.

8. A method as defined in claim 1, in which the electrodes are a pair of disc electrodes, and are first moulded into the surface of an insulating plate or pad, the plate or pad being subsequently applied to the skin.

9. A method as defined in claim 1, in which the electrodes are independently applied to the skin.

10. A method as defined in claim 1, in which said electrical signal is a D.C. signal having a square wave waveform.

* * * * *